(12) United States Patent  
Schmidt et al.

(10) Patent No.: US 7,611,856 B2
(45) Date of Patent: Nov. 3, 2009

(54) MASS SPECTROMETRY-BASED METHODS FOR DETECTION AND DIFFERENTIATION OF BOTULINUM NEUROTOXINS

(75) Inventors: Jurgen G. Schmidt, Los Alamos, NM (US); Anne E. Boyer, Atlanta, GA (US); Suzanne R. Kalb, Atlanta, GA (US); Hercules Moura, Tucker, GA (US); John R. Barr, Suwannee, GA (US); Adrian R. Woolfitt, Atlanta, GA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 180 days.

(21) Appl. No.: 10/980,346

(22) Filed: Nov. 3, 2004

(65) Prior Publication Data

US 2006/0024763 A1 Feb. 2, 2006

Related U.S. Application Data

(60) Provisional application No. 60/517,792, filed on Nov. 5, 2003.

(51) Int. Cl.
*G01N 30/72* (2006.01)
(52) U.S. Cl. .................................... 435/7.72
(58) Field of Classification Search ........................ None
See application file for complete search history.

(56) References Cited

U.S. PATENT DOCUMENTS

| | | | |
|---|---|---|---|
| 5,965,699 A | 10/1999 | Schmidt et al. | 530/326 |
| 6,504,006 B1 | 1/2003 | Shine et al. | 530/323 |
| 6,762,280 B2 * | 7/2004 | Schmidt et al. | 530/300 |
| 6,803,475 B2 | 10/2004 | Wipf et al. | 556/465 |

FOREIGN PATENT DOCUMENTS

| | | |
|---|---|---|
| WO | WO03001206 | 1/2003 |
| WO | WO 03001206 A1 * | 1/2003 |

OTHER PUBLICATIONS

Kalb et al. (Anal. Biochem., 351:84-92, 2006).*
Boyer et al. (Anal. Chem., 77:3916-3924, 2005).*
Schmidt et al., Anal. Biochem., 296:130-137, 2001.*
Schmidt and Stafford (Appl. Environ. Microbiol., 69:297-303, 2003).*
Hortin et al. (Clin. Chem., 47:215-222, 2001).*
Bowers et al. (Anal. Chem., 65:475R-479R, 1993).*
Schmidt et al., Appl. Microbiol., v69 (1) pp. 297-303 (2003).

* cited by examiner

*Primary Examiner*—Robert B Mondesi
*Assistant Examiner*—Brian J Gangle
(74) *Attorney, Agent, or Firm*—Bruce H. Cottrell; Juliet A. Jones

(57) ABSTRACT

The present invention is directed to a method for detecting the presence of clostridial neurotoxins in a sample by mixing a sample with a peptide that can serve as a substrate for proteolytic activity of a clostridial neurotoxin; and measuring for proteolytic activity of a clostridial neurotoxin by a mass spectroscopy technique. In one embodiment, the peptide can have an affinity tag attached at two or more sites.

13 Claims, 3 Drawing Sheets

Figure 1: shows the mass spectrometry data of the peptide Biotin – KGSNRTRIDEANQRATRMLGGK-Biotin (upper) and the result of exposure to BoNT A showing the 2 distinct products of the specific cleavage of the peptide

LC-ESI-MS/MS Quantification of CT BoNT-A Product $y = 0.0147x + 1.1222$
$R^2 = 0.9907$ ♦ CT-Product
■ NT-Product $y = 0.0128x + 0.3538$
$R^2 = 0.9907$

FIG. 3

SEQUENCE LISTING

```
<160> NUMBER OF SEQ ID NOS: 55

<210> SEQ ID NO 1
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(22)
<223> OTHER INFORMATION: Biotin bound at each terminus of protein

<400> SEQUENCE: 1

Lys Gly Ser Asn Arg Thr Arg Ile Asp Glu Ala Asn Gln Arg Ala Thr
1               5                   10                  15

Arg Met Leu Gly Gly Lys
            20

<210> SEQ ID NO 2
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a a Botulinum Neurotoxin (BoNT)
<220> FEATURE:
<221> NAME/KEY: MISC_FEATURE
<222> LOCATION: (1)..(22)
<223> OTHER INFORMATION: Biotin bound at each terminus of protein
<220> FEATURE:
<221> NAME/KEY: MISC_FEATURE
<222> LOCATION: (18)..()
OTHER INFORMATION: Xaa can represent either Nle or Met

SEQUENCE: 2

Lys Gly Ser Asn Arg Thr Arg Ile Asp Gln Gly Asn Gln Arg Ala Thr
1               5                   10                  15
```

Arg Xaa Leu Gly Gly Lys
            20

<210> SEQ ID NO 3
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(22)
<223> OTHER INFORMATION: Biotin bound at each terminus of protein
<220> FEATURE:
<221> NAME/KEY: MISC_FEATURE
<222> LOCATION: (8)..()
<223> OTHER INFORMATION: Ile at no. 8 includes additional 7 amu's
<220> FEATURE:
<221> NAME/KEY: MISC_FEATURE
<222> LOCATION: (15)..()
<223> OTHER INFORMATION: Alanine at no. 15 includes additional 7 amu's
<220> FEATURE:
<221> NAME/KEY: MISC_FEATURE
<222> LOCATION: (18)..()
<223> OTHER INFORMATION: Xaa can represent either Nle or Met

<400> SEQUENCE: 3

Lys Gly Ser Asn Arg Thr Arg Ile Asp Gln Gly Asn Gln Arg Ala Thr
1               5                   10                  15

Arg Xaa Leu Gly Gly Lys
            20

<210> SEQ ID NO 4
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(22)
<223> OTHER INFORMATION: Biotin bound at each terminus of protein
<220> FEATURE:
<221> NAME/KEY: MISC_FEATURE
<222> LOCATION: (18)..()
<223> OTHER INFORMATION: Xaa can represent either Nle or Met

<400> SEQUENCE: 4

Lys Gly Ser Asn Arg Thr Arg Ile Asp Glu Gly Asn Gln Arg Ala Thr
1               5                   10                  15

Arg Xaa Leu Gly Gly Lys
            20

<210> SEQ ID NO 5
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (8)..()
<223> OTHER INFORMATION: Ile at no. 8 includes additional 7 amu's
<220> FEATURE:
<221> NAME/KEY: MISC_FEATURE
<222> LOCATION: (15)..()
<223> OTHER INFORMATION: Alanine at no. 15 includes additional 7 amu's
<220> FEATURE:
<221> NAME/KEY: MISC_FEATURE

```
<222> LOCATION: (18)..()
<223> OTHER INFORMATION: Xaa can represent either Nle or Met

<400> SEQUENCE: 5

Lys Gly Ser Asn Arg Thr Arg Ile Asp Glu Gly Asn Gln Arg Ala Thr
1               5                   10                  15

Arg Xaa Leu Gly Gly Lys
            20

<210> SEQ ID NO 6
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 6

Ser Asn Lys Thr Arg Ile Asp Glu Ala Asn Gln Arg Ala Thr Lys Met
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 7

Ser Asn Arg Thr Arg Ile Asp Gln Gly Asn Gln Arg Ala Thr Arg Met
1               5                   10                  15

Leu

<210> SEQ ID NO 8
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 8

Ser Asn Arg Thr Arg Ile Asp Gln Gly Asn Gln Arg Gly Thr Arg Met
1               5                   10                  15

Leu

<210> SEQ ID NO 9
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT).

<400> SEQUENCE: 9

Ser Asn Arg Thr Arg Ile Asp Gln Ala Asn Arg Gln Ala Thr Arg Met
1               5                   10                  15

Leu

<210> SEQ ID NO 10
<211> LENGTH: 17
<212> TYPE: PRT
```

```
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (16)..()
<223> OTHER INFORMATION: Xaa can represent either Nle or Met

<400> SEQUENCE: 10

Ser Asn Arg Thr Arg Ile Asp Gln Ala Asn Gln Arg Ala Thr Arg Xaa
1               5                   10                  15

Leu

<210> SEQ ID NO 11
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (16)..()
<223> OTHER INFORMATION: Xaa can represent either Nle or Met

<400> SEQUENCE: 11

Ser Asn Arg Thr Arg Ile Asp Glu Gly Asn Gln Arg Ala Thr Arg Xaa
1               5                   10                  15

Leu

<210> SEQ ID NO 12
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (16)..()
<223> OTHER INFORMATION: Xaa can represent either Nle or Met

<400> SEQUENCE: 12

Ser Asn Arg Thr Arg Ile Asp Gln Gly Asn Gln Arg Gly Thr Arg Xaa
1               5                   10                  15

Leu

<210> SEQ ID NO 13
<211> LENGTH: 39
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(39)
<223> OTHER INFORMATION: Biotin bound at each terminus of protein

<400> SEQUENCE: 13

Lys Gly Leu Ser Glu Leu Asp Asp Arg Ala Asp Ala Leu Gln Ala Gly
1               5                   10                  15

Ala Ser Gln Phe Glu Thr Ser Ala Ala Lys Leu Lys Arg Lys Tyr Trp
                20                  25                  30

Trp Lys Asn Leu Gly Gly Lys
            35
```

```
<210> SEQ ID NO 14
<211> LENGTH: 35
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 14

Leu Ser Glu Leu Asp Asp Arg Ala Asp Ala Leu Gln Ala Gly Ala Ser
1               5                   10                  15

Gln Phe Glu Thr Ser Ala Ala Lys Leu Lys Arg Lys Tyr Trp Trp Lys
            20                  25                  30

Asn Leu Lys
        35

<210> SEQ ID NO 15
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 15

Leu Ser Glu Leu Asp Asp Arg Ala Asp Ala Leu Gln Ala Gly Ala Ser
1               5                   10                  15

Gln

<210> SEQ ID NO 16
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (8)..()
<223> OTHER INFORMATION: Alanine at no. 8 includes additional 7 amu's

<400> SEQUENCE: 16

Leu Ser Glu Leu Asp Asp Arg Ala Asp Ala Leu Gln Ala Gly Ala Ser
1               5                   10                  15

Gln

<210> SEQ ID NO 17
<211> LENGTH: 16
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 17

Leu Ser Glu Leu Asp Asp Arg Ala Asp Ala Leu Gln Ala Gly Ala Ser
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
```

```
<220> FEATURE:
<221> NAME/KEY: MISC_FEATURE
<222> LOCATION: (8)..()
<223> OTHER INFORMATION: Alanine at no. 8 includes additional 7 amu's

<400> SEQUENCE: 18

Leu Ser Glu Leu Asp Asp Arg Ala Asp Ala Leu Gln Ala Gly Ala Ser
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 19

Phe Glu Thr Ser Ala Ala Lys Leu Lys Arg Lys Tyr Trp Trp Lys Asn
1               5                   10                  15

Leu Lys

<210> SEQ ID NO 20
<211> LENGTH: 18
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (5)..()
<223> OTHER INFORMATION: Alanine at no. 5 includes additional 7 amu's

<400> SEQUENCE: 20

Phe Glu Thr Ser Ala Ala Lys Leu Lys Arg Lys Tyr Trp Trp Lys Asn
1               5                   10                  15

Leu Lys

<210> SEQ ID NO 21
<211> LENGTH: 39
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 21

Ala Gln Val Asp Glu Val Val Asp Ile Met Arg Val Asn Val Asp Lys
1               5                   10                  15

Val Leu Glu Arg Asp Gln Lys Leu Ser Glu Leu Asp Asp Arg Ala Asp
            20                  25                  30

Ala Leu Gln Ala Gly Ala Ser
        35

<210> SEQ ID NO 22
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 22

Lys Leu Ser Glu Leu Asp Asp Arg Ala Asp Ala Leu Gln Ala Gly Ala
1               5                   10                  15
```

```
<210> SEQ ID NO 23
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (9)..()
<223> OTHER INFORMATION: Alanine at no. 9 includes additional 7 amu's

<400> SEQUENCE: 23

Lys Leu Ser Glu Leu Asp Asp Arg Ala Asp Ala Leu Gln Ala Gly Ala
1               5                   10                  15

Ser

<210> SEQ ID NO 24
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 24

Ala Gln Val Asp Glu Val Val Asp Ile Met Arg Val Asn Val Asp Lys
1               5                   10                  15

Val Leu Glu Arg Asp Gln
            20

<210> SEQ ID NO 25
<211> LENGTH: 22
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 25

Ala Gln Val Asp Glu Val Val Asp Ile Met Arg Val Asn Val Asp Lys
1               5                   10                  15

Val Leu Glu Arg Asp Gln
            20

<210> SEQ ID NO 26
<211> LENGTH: 23
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 26

Ala Gln Val Asp Glu Val Val Asp Ile Met Arg Val Asn Val Asp Lys
1               5                   10                  15

Val Leu Glu Arg Asp Gln Lys
            20

<210> SEQ ID NO 27
<211> LENGTH: 23
<212> TYPE: PRT
<213> ORGANISM: Artificial Sequence
```

```
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..()
<223> OTHER INFORMATION: Alanine at no. 1 includes additional 7 amu's

<400> SEQUENCE: 27

Ala Gln Val Asp Glu Val Val Asp Ile Met Arg Val Asn Val Asp Lys
1               5                   10                  15

Val Leu Glu Arg Asp Gln Lys
            20

<210> SEQ ID NO 28
<211> LENGTH: 31
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 28

Ile Ile Gly Asn Leu Arg His Met Ala Leu Asp Met Gly Asn Glu Ile
1               5                   10                  15

Asp Thr Gln Asn Arg Gln Ile Asp Arg Ile Met Glu Lys Ala Asp
            20                  25                  30

<210> SEQ ID NO 29
<211> LENGTH: 25
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)

<400> SEQUENCE: 29

Ile Ile Gly Asn Leu Arg His Met Ala Leu Asp Met Gly Asn Glu Ile
1               5                   10                  15

Asp Thr Gln Asn Arg Gln Ile Asp Arg
            20                  25

<210> SEQ ID NO 30
<211> LENGTH: 25
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (9)..()
<223> OTHER INFORMATION: Alanine at no. 9 includes additional 7 amu's

<400> SEQUENCE: 30

Ile Ile Gly Asn Leu Arg His Met Ala Leu Asp Met Gly Asn Glu Ile
1               5                   10                  15

Asp Thr Gln Asn Arg Gln Ile Asp Arg
            20                  25

<210> SEQ ID NO 31
<211> LENGTH: 6
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
```

-continued

```
<400> SEQUENCE: 31

Ile Met Glu Lys Ala Asp
1               5

<210> SEQ ID NO 32
<211> LENGTH: 6
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (5)..()
<223> OTHER INFORMATION: Alanine at no. 8 includes additional 7 amu's

<400> SEQUENCE: 32

Ile Met Glu Lys Ala Asp
1               5

<210> SEQ ID NO 33
<211> LENGTH: 36
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (35)..()
<223> OTHER INFORMATION: Xaa can represent either Nle or Met

<400> SEQUENCE: 33

Ile Glu Tyr Asn Val Glu His Ala Val Asp Tyr Val Glu Arg Ala Val
1               5                   10                  15

Ser Asp Thr Lys Lys Ala Val Lys Tyr Gln Ser Lys Ala Arg Arg Lys
                20                  25                  30

Lys Ile Xaa Ile
        35

<210> SEQ ID NO 34
<211> LENGTH: 36
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (35)..()
<223> OTHER INFORMATION: Xaa can represent either Nle or Met

<400> SEQUENCE: 34

Ile Glu Tyr Asn Val Glu His Ala Val Asp Tyr Val Glu Arg Ala Val
1               5                   10                  15

Ser Asp Thr Lys Lys Ala Val Arg Tyr Gln Ser Lys Ala Arg Arg Lys
                20                  25                  30

Lys Ile Xaa Ile
        35

<210> SEQ ID NO 35
<211> LENGTH: 36
<212> TYPE: PRT
<213> ORGANISM: Artificial Sequence
<220> FEATURE:
<223> OTHER INFORMATION: synthetic peptide chosen such that it is
```

```
        cleaved by a Botulinum Neurotoxin (BoNT)
<220> FEATURE:
<221> NAME/KEY: MISC_FEATURE
<222> LOCATION: (35)..()
<223> OTHER INFORMATION: Xaa can represent either Nle or Met

<400> SEQUENCE: 35

Ile Glu Tyr Asn Val Glu His Ala Val Asp Tyr Val Glu Arg Ala Val
1               5                   10                  15

Ser Gln Thr Lys Lys Ala Val Arg Tyr Gln Ser Lys Ala Arg Arg Lys
            20                  25                  30

Lys Ile Xaa Ile
        35

<210> SEQ ID NO 36
<211> LENGTH: 36
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (35)..()
<223> OTHER INFORMATION: Xaa can represent either Nle or Met

<400> SEQUENCE: 36

Ile Glu Tyr Asn Val Glu His Ala Val Asp Tyr Val Glu Arg Ala Val
1               5                   10                  15

Ser Gln Ser Lys Lys Ala Val Arg Tyr Gln Ser Lys Ala Arg Arg Lys
            20                  25                  30

Lys Ile Xaa Ile
        35

<210> SEQ ID NO 37
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(17)
<223> OTHER INFORMATION: amide bound at one end of the peptide

<400> SEQUENCE: 37

Ser Asn Lys Thr Arg Ile Asp Glu Ala Asn Gln Arg Ala Thr Lys Met
1               5                   10                  15

Leu

<210> SEQ ID NO 38
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (1)..(17)
<223> OTHER INFORMATION: amide bound at one end of the peptide

<400> SEQUENCE: 38

Ser Asn Arg Thr Arg Ile Asp Glu Ala Asn Gln Arg Ala Thr Arg Met
1               5                   10                  15
```

Leu

<210> SEQ ID NO 39
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (17)..()
<223> OTHER INFORMATION: lysine MAP4 structure tree (4K2KC(Beta)A) is
      bound at the C-end
<220> FEATURE:
<221> NAME/KEY: MISC_FEATURE
<222> LOCATION: (16)..()
<223> OTHER INFORMATION: Xaa can represent either Nle or Met

<400> SEQUENCE: 39

Ser Asn Arg Thr Arg Ile Asp Gln Gly Asn Gln Arg Ala Thr Arg Xaa
1               5                   10                  15

Leu

<210> SEQ ID NO 40
<211> LENGTH: 13
<212> TYPE: PRT
<213> ORGANISM: Artificial Sequence
<220> FEATURE:
<223> OTHER INFORMATION: Fragment resulting from cleavage of substrate 1
      by a Botulinum Neurotoxin (BoNT)
<220> FEATURE:
<221> NAME/KEY: MISC_FEATURE
<223> OTHER INFORMATION: Biotin bound at the N- terminus of the
      protein fragment

<400> SEQUENCE: 40

Lys Gly Ser Asn Arg Thr Arg Ile Asp Glu Ala Asn Gln
1               5                   10

<210> SEQ ID NO 41
<211> LENGTH: 9
<212> TYPE: PRT
<213> ORGANISM: Artificial Sequence
<220> FEATURE:
<223> OTHER INFORMATION: Fragment resulting from cleavage of substrate 1
      by a Botulinum Neurotoxin (BoNT)
<220> FEATURE:
<221> NAME/KEY: MISC_FEATURE
<223> OTHER INFORMATION: Biotin bound at the C- terminus of the protein
      fragment

<400> SEQUENCE: 41

Arg Ala Thr Arg Met Leu Gly Gly Lys
1               5

<210> SEQ ID NO 42
<211> LENGTH: 14
<212> TYPE: PRT
<213> ORGANISM: Artificial Sequence
<220> FEATURE:
<223> OTHER INFORMATION: Fragment resulting from cleavage of substrate 1
      by a Botulinum Neurotoxin (BoNT)
<220> FEATURE:
<221> NAME/KEY: MISC_FEATURE
<223> OTHER INFORMATION: Biotin bound at the N- terminus of the protein
      fragment

<400> SEQUENCE: 42

Lys Gly Ser Asn Arg Thr Arg Ile Asp Glu Ala Asn Gln Arg

-continued

```
1               5                   10
```

```
<210> SEQ ID NO 43
<211> LENGTH: 8
<212> TYPE: PRT
<213> ORGANISM: Artificial Sequence
<220> FEATURE:
<223> OTHER INFORMATION: Fragment resulting from cleavage of substrate 1
      by a Botulinum Neurotoxin (BoNT)
<220> FEATURE:
<221> NAME/KEY: MISC_FEATURE
<223> OTHER INFORMATION: Biotin bound at the C- terminus of the protein
      fragment.

<400> SEQUENCE: 43

Ala Thr Arg Met Leu Gly Gly Lys
1               5

<210> SEQ ID NO 44
<211> LENGTH: 25
<212> TYPE: PRT
<213> ORGANISM: Artificial Sequence
<220> FEATURE:
<223> OTHER INFORMATION: Fragment resulting from cleavage of substrate
      28 by a Botulinum Neurotoxin (BoNT)

<400> SEQUENCE: 44

Ile Ile Gly Asn Leu Arg His Met Ala Leu Asp Met Gly Asn Glu Ile
1               5                   10                  15

Asp Thr Gln Asn Arg Gln Ile Asp Arg
            20                  25

<210> SEQ ID NO 45
<211> LENGTH: 6
<212> TYPE: PRT
<213> ORGANISM: Artificial Sequence
<220> FEATURE:
<223> OTHER INFORMATION: Fragment resulting from cleavage of substrate
      28 by a Botulinum Neurotoxin (BoNT)

<400> SEQUENCE: 45

Ile Met Glu Lys Ala Asp
1               5

<210> SEQ ID NO 46
<211> LENGTH: 17
<212> TYPE: PRT
<213> ORGANISM: Artificial Sequence
<220> FEATURE:
<223> OTHER INFORMATION: Fragment resulting from cleavage of substrate
      14 by a Botulinum Neurotoxin (BoNT)

<400> SEQUENCE: 46

Leu Ser Glu Leu Asp Asp Arg Ala Asp Ala Leu Gln Ala Gly Ala Ser
1               5                   10                  15

Gln

<210> SEQ ID NO 47
<211> LENGTH: 18
<212> TYPE: PRT
<213> ORGANISM: Artificial Sequence
<220> FEATURE:
<223> OTHER INFORMATION: Fragment resulting from cleavage of substrate
      14 by a Botulinum Neurotoxin (BoNT)

<400> SEQUENCE: 47

Phe Glu Thr Ser Ala Ala Lys Leu Lys Arg Lys Tyr Trp Trp Lys Asn
```

```
<210> SEQ ID NO 48
<211> LENGTH: 23
<212> TYPE: PRT
<213> ORGANISM: Artificial Sequence
<220> FEATURE:
<223> OTHER INFORMATION: Fragment resulting from cleavage of substrate
      21 by a Botulinum Neurotoxin (BoNT)

<400> SEQUENCE: 48

Ala Gln Val Asp Glu Val Val Asp Ile Met Arg Val Asn Val Asp Lys
1               5                   10                  15

Val Leu Glu Arg Asp Gln Lys
            20

<210> SEQ ID NO 49
<211> LENGTH: 16
<212> TYPE: PRT
<213> ORGANISM: Artificial Sequence
<220> FEATURE:
<223> OTHER INFORMATION: Fragment resulting from cleavage of substrate
      21 by a Botulinum Neurotoxin (BoNT)

<400> SEQUENCE: 49

Leu Ser Glu Leu Asp Asp Arg Ala Asp Ala Leu Gln Ala Gly Ala Ser
1               5                   10                  15

<210> SEQ ID NO 50
<211> LENGTH: 22
<212> TYPE: PRT
<213> ORGANISM: Artificial Sequence
<220> FEATURE:
<223> OTHER INFORMATION: Fragment resulting from cleavage of substrate
      21 by a Botulinum Neurotoxin (BoNT)

<400> SEQUENCE: 50

Ala Gln Val Asp Glu Val Val Asp Ile Met Arg Val Asn Val Asp Lys
1               5                   10                  15

Val Leu Glu Arg Asp Gln
            20

<210> SEQ ID NO 51
<211> LENGTH: 17
<212> TYPE: PRT
<213> ORGANISM: Artificial Sequence
<220> FEATURE:
<223> OTHER INFORMATION: Fragment resulting from cleavage of substrate
      21 by a Botulinum Neurotoxin (BoNT)

<400> SEQUENCE: 51

Lys Leu Ser Glu Leu Asp Asp Arg Ala Asp Ala Leu Gln Ala Gly Ala
1               5                   10                  15

Ser

<210> SEQ ID NO 52
<211> LENGTH: 12
<212> TYPE: PRT
<213> ORGANISM: Artificial Sequence
<220> FEATURE:
<223> OTHER INFORMATION: Internal Standard
<220> FEATURE:
<221> NAME/KEY: MISC_FEATURE
<223> OTHER INFORMATION: Biotin bound at the C- terminus of protein
      fragment
```

```
<220> FEATURE:
<221> NAME/KEY: MISC_FEATURE
<222> LOCATION: (12)..()
<223> OTHER INFORMATION: Biotin bound at no. 12 of protein fragment

<400> SEQUENCE: 52

Leu Arg Thr Ala Gln Ala Asp Ile Thr Asn Ser Lys
1               5                   10

<210> SEQ ID NO 53
<211> LENGTH: 17
<212> TYPE: PRT
<213> ORGANISM: Artificial Sequence
<220> FEATURE:
<223> OTHER INFORMATION: synthetic peptide chosen such that it is
      cleaved by a Botulinum Neurotoxin (BoNT)
<220> FEATURE:
<221> NAME/KEY: MISC_FEATURE
<222> LOCATION: (16)..()
<223> OTHER INFORMATION: X = Norleucine
<220> FEATURE:
<221> NAME/KEY: misc_feature
<222> LOCATION: (16)..(16)
<223> OTHER INFORMATION: Xaa can be any naturally occurring amino acid

<400> SEQUENCE: 53

Ser Asn Arg Thr Arg Ile Asp Gln Gly Asn Gln Arg Ala Thr Arg Xaa
1               5                   10                  15

Leu

<210> SEQ ID NO 54
<211> LENGTH: 11
<212> TYPE: PRT
<213> ORGANISM: Artificial Sequence
<220> FEATURE:
<223> OTHER INFORMATION: Fragment resulting from cleavage of substrate
      40 by a Botulinum Neurotoxin (BoNT)

<400> SEQUENCE: 54

Ser Asn Arg Thr Arg Ile Asp Gln Gly Asn Gln
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Fragment resulting from cleavage of substrate
      40 by a Botulinum Neurotoxin (BoNT)
<220> FEATURE:
<221> NAME/KEY: MISC_FEATURE
<222> LOCATION: (5)..()
<223> OTHER INFORMATION: X=Norleucine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 55

Arg Ala Thr Arg Xaa Leu
1               5
```

MASS SPECTROMETRY-BASED METHODS FOR DETECTION AND DIFFERENTIATION OF BOTULINUM NEUROTOXINS

RELATED APPLICATIONS

This application claims the benefit of the filing of U.S. provisional application 60/517,792 filed Nov. 5, 2003.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to detection methods for botulinum neurotoxins and to mass spectrometry-based methods for detection and differentiation of botulinum neurotoxins.

BACKGROUND OF THE INVENTION

The neurotoxins produced by *Clostridium botulinum* (Botulinum Neurotoxins, BoNT) are among the most poisonous substances known. There are seven distinct serotypes of BoNTs (A-G), four of which are generally found to cause botulism in humans (A, B, E and F). There are several challenges in the diagnosis and treatment of botulism. Since the toxicity of BoNT is so great, it is necessary that BoNT can be detected at very low concentrations, preferably as the active toxin. The identification of the serotype is important for the most effective treatment. It is also imperative that the diagnosis be made rapidly since the equine-based treatment can have several substantial side effects.

The current standard for detecting botulinum toxins in, e.g., food, is the mouse lethality bioassay. Not only does this process require the use of animals, but also the process takes nearly a week to complete.

The current methods for detecting BoNT include a mouse bioassay and an enzyme-linked immunosorbent assay (ELISA). The mouse bioassay is currently the gold standard and is the only widely accepted method for the detection of BoNT. Mixtures of neutralizing antibodies are given to mice in conjunction with the sample in question to differentiate the toxin serotype. Mice receiving the appropriate anti-BoNT serotype antibody along with the toxic sample do not show symptoms and survive, while mice treated with the other serotype antibodies show symptoms and die. Importantly, this assay measures only active toxin. The mouse bioassay is very sensitive, detecting as little as 10 picograms (pg) of active toxin which is defined as 1 mouse $LD_{50}$ or 1 unit of BoNT. However, the mouse bioassay can be slow (taking up to 4 days) for final results and it requires the sacrifice of many animals. It is highly desirable to have a more rapid technique of detecting botulinum toxins.

The ELISA is much more rapid, but is less sensitive, is problematic in certain matrices, shows cross reactivity between BoNT serotypes, and measures inactive toxin along with active toxin. The ELISA is currently used primarily as a fast screening technique and results are verified by the mouse bioassay.

Among recent approaches are: (1) U.S. Pat. No. 5,965,699 by Schmidt et al. wherein an assay for the proteolytic activity of type A botulinum toxin is described involving addition of a fluorigenic reagent that reacts with one of the proteolytic products to yield a fluorescent product that can be detected; and, (2) U.S. Pat. No. 6,762,280 by Schmidt et al. wherein assays for the proteolytic activity of clostridal neurotoxins are described involving synthetic peptide substrates modified with signal moieties such as fluorescent molecules for eventual signal output by a proteolytic product. Shine et al. describe still another fluorescence based detection method for botulinum neurotoxins in U.S. Pat. No. 6,504,006. Fluorescence arrays can however produce fluorescence response from unspecific cleavage of the substrate by other proteases than clostridal toxins.

Applicants have now developed a detection and differentiation method for botulinum neurotoxins based upon mass spectroscopy analysis of proteolytic products. The method can also allow for quantification of amounts of toxin and unequivocal product identification due to specific botulinum toxin cleavage of substrate.

It is an object of the present invention to provide such a detection and differentiation method for botulinum neurotoxins.

SUMMARY OF THE INVENTION

In accordance with the purposes of the present invention, as embodied and broadly described herein, the present invention provides a method for detecting the presence of botulinum neurotoxins in a sample including mixing a sample with a peptide that can serve as a substrate for proteolytic activity of a botulinum neurotoxin, and measuring for proteolytic activity of a botulinum neurotoxin by a mass spectroscopy technique. In one embodiment, the method can further provide a quantification or determination of the amount of toxin present.

The present invention further provides a method for detecting the presence of botulinum neurotoxins in a sample and differentiating among types of botulinum neurotoxins, the process including mixing a sample with a peptide that can serve as a substrate for proteolytic activity of a botulinum neurotoxin, and measuring for proteolytic activity of a botulinum neurotoxin by a mass spectroscopy technique

BRIEF DESCRIPTION OF THE DRAWINGS

FIG. 3 depicts an LC-ESI-MS/MS calibration curve for quantitation of CT (C-terminus) and NT (N-terminus) peptides resulting from cleavage of a substrate by the BoNT-A serotype of the clostridial neurotoxin, as described herein. The x-axis represents the concentration of the BoNT-A-substrate complex and the y-axis represents the calculated concentration of the cleaved peptides.

DETAILED DESCRIPTION

Figure 1:
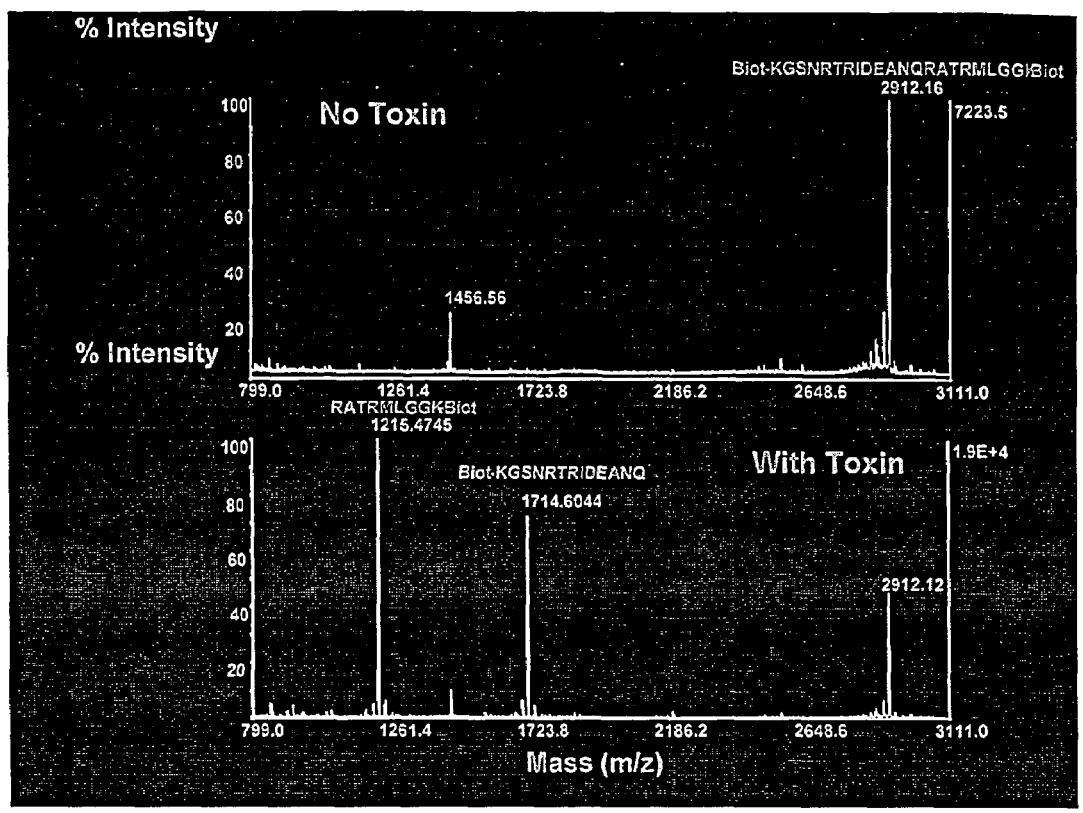
FIG. 1 shows the mass spectroscopy data for both: (*a*) a sample of a specific peptide; and (*b*) a sample of the specific peptide after mixing with a sample of BoNT serotype A.

The present invention is concerned with mass spectrometry-based methods for detection of botulinum neurotoxins (BoNTs). Further, the present invention is concerned with mass spectrometry-based methods for detection and differentiation among botulinum neurotoxins (BoNTs). The method can further provide a quantification or determination of the amount of toxin and serotype present.

In the past few years, mass spectrometry (MS)-based methods have emerged as fast and accurate tools to detect and identify a wide range of biomarkers.

A rapid and accurate method for the detection and differentiation of BoNTs has now been developed which utilizes the high specificity of the enzymatic toxin with the high specificity of mass spectroscopy (MS). This MS-based method allows the detection of enzymatic activity of all the BoNT serotypes and those include the A, B, E and F serotypes that are the serotypes of most interest due to their potential threat to humans.

This MS-based method can be extended to other proteolytic cleavage proteins within the Clostridium family as well as to tularemia. Synthetic peptide substrates have been developed for the specific endopeptidase activities of BoNTs, based on the sequences of the natural protein substrates SNAP-25 (a synaptosome-associated protein) and VAMP-2 (a vesicle-associated membrane protein). Since each BoNT serotype has a unique cleavage site on a unique peptide, specific product peptides can de detected by mass spectrometry and differentiate among the active BoNT serotypes. In the method of the present invention, a target sample can be mixed with the peptide serving as a substrate for proteolytic activity of a botulinum neurotoxin. After a digestion period of from a few minutes to a few hours, preferably from about 30 minutes to about 2 hours, the product peptides (both an N-terminated fragment and a C-terminated fragment) can be recovered from any matrix using affinity tags on the substrate peptide and therefore unequivocally identified and quantified by mass spectroscopy.

Suitable mass spectrometry techniques can include matrix-assisted laser desorption-ionization time of flight mass spectrometry (MALDI-TOF-MS) and high performance liquid chromatography-electrospray ionization-tandem mass spectrometry (LC-ESI-MS/MS). Other mass spectroscopy techniques may also be employed for analysis of the BoNT product peptides. MS-based techniques such as MALDI-TOF-MS can allow screening of hundreds of samples per hour for BoNT enzymatic activity. While LC-ESI-MS/MS is much slower than MALDI-TOF-MS, it still offers high specificity and sensitivity and allows accurate quantitative measurements of the levels of BoNT. The MALDI-TOF-MS screening method has been used to detect specific fragments of peptides cleaved by BoNT A, B, E and F in a pure reaction buffer or within various environmental and clinical type matrices such as milk, sausage, serum and stool spiked with A, B and E light chain (about 50 kDa) and A and F toxin complexes (about 500 and 900 kDa respectively).

The high specificity of the present invention has been verified by testing a mixture of the substrate peptides with each of the BoNT serotypes. In each case, only the specific and expected products from the particular serotype were detected. An assay using the method of the present invention could detect activity as low as 5 picograms per milliliter (pg/ml) of toxin in total sample volumes of about 20 microliters. The present method has been demonstrated to be fast, sensitive and specific and can be used as a high-throughput assay for the detection and quantification of BoNT activity in a variety of sample types.

Within various embodiments of the present invention, the substrate can be any peptide or protein that can serve as a substrate for the proteolytic activity of the target neurotoxin, especially the clostridial neurotoxins. Among suitable substrates are substrates similar to those described by Schmidt et al. in U.S. Pat. No. 6,762,280, in particular, the substrates described in columns 5-8 with the exception that signal (fluorescence) labels such as the S-(fluoresceinyl)-cysteine and quenching labels such as N(epsilon)-(2,4-dinitrophenyl)-lysine are unnecessary and can be any suitable amino acid that leaves the cleavage site unaffected. The substrates as described by Schmidt et al. in those columns are hereby incorporated by reference. In a substrate of the present invention, a final substrate (1) Biotin-KGSNRTRIDEAN-QRATRMLGGK-biotin was constructed. Substrate (1) (SEQ ID NO: 1) included the following peptide with biotin bound at both ends of the peptide:

```
1  2  3  4  5  6  7  8  9  10 11 12 13 14 15 16 17 18 19
K  G  S  N  R  T  R  I  D  E  A  N  Q  R  A  T  R  M  L 20 21 22
G  G  K.
```

The cleavage site remains the same as in substrate (1) of Schmidt et al. at column 5.

Other substrates for BoNT A and BoNT C were constructed and included substrate (2) BiotinKG SNR-TRIDQGNQRATRNleLGGKBiotin (SEQ ID NO: 2), substrate 3 BiotinKGSNRTR(I+7)DQGNQR(A+7)TRNleLGGKBiotin (SEQ ID NO: 3), substrate 4 BiotinKGSNRTRIDEGNQRATRNleLGGKBiotin (SEQ ID NO: 4), and substrate 5 BiotinKGSNRTR(I+7)DEGNQR(A+7)TRNleLGGKBiotin (SEQ ID NO: 5). Examples of non-biotinylated substrates for BoNT A and BoNT C can include substrate 6 SNKTRIDEANQRATKML (SEQ ID NO: 6), substrate 7 SNRTRIDQGNQRATRML (SEQ ID NO: 7), substrate 8 NRTRIDQGNQRGTRML (SEQ ID NO: 8), substrate 9 SNRTRIDQANRQATRML (SEQ ID NO: 9), substrate 10 SNRTRIDQANQRATRNleL (SEQ ID NO: 10), substrate 11 SNRTRIDEGNQRATRNleL (SEQ ID NO: 11), and substrate 12 SNRTRIDQGNQRGTRNleL (SEQ ID NO:

12). Substrate (2) (SEQ ID NO: 2) included the following peptide with biotin bound at both ends of the peptide:

```
1 2 3 4 5 6 7 8 9 10 11 12 13 14 15 16 17 18 19 20 21 22
K G S N R T R I D Q  G  N  Q  R  A  T  R  M  L  G  G  K
```

In this substrate at 18, Norleucine (Nle) is substituted for Methionine (M),

```
1 2 3 4 5 6 7 8 9 10 11 12 13 14 15 16 17 18  19 20 21 22   (SEQ ID NO: 58).
K G S N R T R I D Q  G  N  Q  R  A  T  R  Nle L  G  G  K
```

Substrate (3) (SEQ ID NO: 3) included the following peptide with biotin bound at both ends of the peptide:

```
1 2 3 4 5 6 7 8      9 10 11 12 13 14 15     16 17 18 19 20 21 22
K G S N R T R (I+7)  D Q  G  N  Q  R  (A+7)  T  R  M  L  G  G  K
```

In this substrate at 18, Norleucine is substituted for Methionine,

```
1 2 3 4 5 6 7 8      9 10 11 12 13 14 15     16 17 18  19 20 21 22   (SEQ ID NO: 59).
K G S N R T R (I+7)  D Q  G  N  Q  R  (A+7)  T  R  Nle L  G  G  K
```

Substrate (4) (SEQ ID NO: 4) included the following peptide with biotin bound at both ends of the peptide:

```
1 2 3 4 5 6 7 8 9 10 11 12 13 14 15 16 17 18 19 20 21 22
K G S N R T R I D E  G  N  Q  R  A  T  R  M  L  G  G  K
```

In this substrate at 18, Norleucine is substituted for Methionine,

```
1 2 3 4 5 6 7 8 9 10 11 12 13 14 15 16 17 18  19 20 21 22 (SEQ ID NO: 60).
K G S N R T R I D E  G  N  Q  R  A  T  R  Nle L  G  G  K
```

Substrate (5) (SEQ ID NO: 5) included the following peptide with biotin bound at both ends of the peptide:

```
1 2 3 4 5 6 7 8      9 10 11 12 13 14 15     16 17 18 19 20 21 22
K G S N R T R (I+7)  D E  G  N  Q  R  (A+7)  T  R  M  L  G  G  K
```

In this substrate at 18, Norleucine is substituted for Methionine,

```
1 2 3 4 5 6 7 8      9 10 11 12 13 14 15     16 17 18  19 20 21 22   (SEQ ID NO: 61).
K G S N R T R (I+7)  D E  G  N  Q  R  (A+7)  T  R  Nle L  G  G  K
```

Substrate (6) (SEQ ID NO: 6) included the following peptide:

```
1 2 3 4 5 6 7 8 9 10 11 12 13 14 15 16 17
S N K T R I D E A N  Q  R  A  T  K  M  L
```

Substrate (7) (SEQ ID NO: 7) included the following peptide:

```
1 2 3 4 5 6 7 8 9 10 11 12 13 14 15 16 17
S N R T R I D Q G N  Q  R  A  T  R  M  L
```

Substrate (8) (SEQ ID NO: 8) included the following peptide:

```
1 2 3 4 5 6 7 8 9 10 11 12 13 14 15 16 17
S N R T R I D Q G N  Q  R  G  T  R  M  L
```

Substrate (9) (SEQ ID NO: 9) included the following peptide:

```
1 2 3 4 5 6 7 8 9 10 11 12 13 14 15 16 17
S N R T R I D Q A N  R  Q  A  T  R  M  L
```

Substrate (10) (SEQ ID NO: 10) included the following peptide:

```
1 2 3 4 5 6 7 8 9 10 11 12 13 14 15 16 17
S N R T R I D Q A N  Q  R  A  T  R  M  L
```

In this substrate at 16, Norleucine is substituted for Methionine,

```
                                    (SEQ ID NO: 62).
1 2 3 4 5 6 7 8 9 10 11 12 13 14 15  16  17
S N R T R I D Q A N  Q  R  A  T  R  Nle  L
```

Substrate (11) (SEQ ID NO: 11) included the following peptide:

```
1 2 3 4 5 6 7 8 9 10 11 12 13 14 15 16 17
S N R T R I D E G N  Q  R  A  T  R  M  L
```

In this substrate at 16, Norleucine is substituted for Methionine,

```
                                    (SEQ ID NO: 63).
1 2 3 4 5 6 7 8 9 10 11 12 13 14 15  16  17
S N R T R I D E G N  Q  R  A  T  R  Nle  L
```

Substrate (12) (SEQ ID NO: 12) included the following peptide:

```
1 2 3 4 5 6 7 8 9 10 11 12 13 14 15 16 17
S N R T R I D Q G N  Q  R  G  T  R  M  L
```

In this substrate at 16, Norleucine is substituted for Methionine,

```
                                    (SEQ ID NO: 64).
1 2 3 4 5 6 7 8 9 10 11 12 13 14 15  16  17
S N R T R I D Q G N  Q  R  G  T  R  Nle  L
```

```
1 2 3 4 5 6 7 8 9 10 11 12 13 14 15 16 17 18 19
K G S N R T R I D Q  G  N  Q  R  A  T  R  M  L
20 21 22
G  G  K
```

In this substrate at 18, Norleucine (Nle) is substituted for Methionine (M).

Substrate (3) (SEQ ID NO: 3) included the following peptide with biotin bound at both ends of the peptide:

```
1 2 3 4 5 6 7 8       9 10 11 12 13 14 15      16
K G S N R T R (I + 7) D  Q  G  N  Q  R  (A + 7) T
17 18 19 20 21 22
R  M  L  G  G  K
```

In this substrate at 18, Norleucine is substituted for Methionine.

Substrate (4) (SEQ ID NO: 4) included the following peptide with biotin bound at both ends of the peptide:

```
1 2 3 4 5 6 7 8 9 10 11 12 13 14 15 16 17 18 19
K G S N R T R I D E  G  N  Q  R  A  T  R  M  L
20 21 22
G  G  K
```

In this substrate at 18, Norleucine is substituted for Methionine.

Substrate (5) (SEQ ID NO: 5) included the following peptide with biotin bound at both ends of the peptide:

```
1 2 3 4 5 6 7 8       9 10 11 12 13 14 15      16
K G S N R T R (I + 7) D  E  G  N  Q  R  (A + 7) T
17 18 19 20 21 22
R  M  L  G  G  K
```

In this substrate at 18, Norleucine is substituted for Methionine.

Substrate (6) (SEQ ID NO: 6) included the following peptide:

```
1 2 3 4 5 6 7 8 9 10 11 12 13 14 15 16 17
S N K T R I D E A N  Q  R  A  T  K  M  L
```

Substrate (7) (SEQ ID NO: 7) included the following peptide:

```
1 2 3 4 5 6 7 8 9 10 11 12 13 14 15 16 17
S N R T R I D Q G N  Q  R  A  T  R  M  L
```

Substrate (8) (SEQ ID NO: 8) included the following peptide:

```
1 2 3 4 5 6 7 8 9 10 11 12 13 14 15 16 17
S N R T R I D Q G N  Q  R  G  T  R  M  L
```

Substrate (9) (SEQ ID NO: 9) included the following peptide:

```
1  2  3  4  5  6  7  8  9  10 11 12 13 14 15 16 17
S  N  R  T  R  I  D  Q  A  N  R  Q  A  T  R  M  L
```

Substrate (10) (SEQ ID NO: 10) included the following peptide:

```
1  2  3  4  5  6  7  8  9  10 11 12 13 14 15 16 17
S  N  R  T  R  I  D  Q  A  N  Q  R  A  T  R  M  L
```

In this substrate at 16, Norleucine is substituted for Methionine.

Substrate (11) (SEQ ID NO: 11) included the following peptide:

```
1  2  3  4  5  6  7  8  9  10 11 12 13 14 15 16 17
S  N  R  T  R  I  D  E  G  N  Q  R  A  T  R  M  L
```

In this substrate at 16, Norleucine is substituted for Methionine.

Substrate (12) (SEQ ID NO: 12) included the following peptide:

```
1  2  3  4  5  6  7  8  9  10 11 12 13 14 15 16 17
S  N  R  T  R  I  D  Q  G  N  Q  R  G  T  R  M  L
```

In this substrate at 16, Norleucine is substituted for Methionine.

Stable isotope labels ($^{13}C_6$, $^{15}N$) Isoleucine and/or ($^{13}C_3$, $^2H_3$, $^{15}N$) Alanine were incorporated as Fmoc protected derivatives into the solid phase synthesis of the peptides. Exemplary of such labeled materials for internal isotope references are the pairs of SNRTRIDQGNQ (SEQ ID NO: 54) and SNRTR(I+7)DQGNQ (SEQ ID NO: 56) (for isoleucine) and RATRNleL SEQ NO: 55) and R(A+7)TRNleL (SEQ ID NO: 57) (for alanine). Other references can readily be prepared as needed. Use of isotope dilution spectroscopy and internal isotope references allow the calibration of the mass spectrometry method and contribute to dramatically improve the sensitivity of the detection method. The labeling position as well as the labeling pattern shown in the example are non-exclusive; other positions and other labeling patterns could be employed to achieve the mass differences suited for isotope dilution spectroscopy and internal isotope references.

Examples of a substrate for a BoNT B include: substrate (13) Biotin-KG-LSELDDRADALQAGASQFETSAAKLKRKYWWKNLGGK-Biotin (SEQ ID NO: 13) and non-biotinylated substrate (14) LSELDDRADALQAGASQFETSAAKLKRKYWWKNLK (SEQ ID NO: 14). Substrate (13) (SEQ ID NO: 13) included the following peptide with biotin bound at both ends of the peptide:

```
1  2  3  4  5  6  7  8  9  10 11 12 13 14 15 16 17 18 19 20
K  G  L  S  E  L  D  D  R  A  D  A  L  Q  A  G  A  S  Q  F 21 22 23 24 25 26 27 28 29 30 31 32 33 34 35
E  T  S  A  A  K  L  K  R  K  Y  W  W  K  N 36 37 38 39
L  G  G  K.
```

Substrate (14) (SEQ ID NO: 14) included the following peptide:

```
1  2  3  4  5  6  7  8  9  10 11 12 13 14 15 16 17 18 19
L  S  E  L  D  D  R  A  D  A  L  Q  A  G  A  S  Q  F  E 20 21 22 23 24 25 26 27 28 29 30 31 32 33 34 35
T  S  A  A  K  L  K  R  K  Y  W  W  K  N  L  K.
```

Other isotope standard pairs employed to calibrate and refine the method can include: substrate (15) LSELDDRADALQAGASQ (SEQ ID NO: 15), substrate (16) LSELDDR(A+7)DALQAGASQ (SEQ ID NO: 16), substrate (17) LSELDDRADALQAGAS (SEQ ID NO: 17), substrate (18) LSELDDR(A+7)DALQAGAS (SEQ ID NO: 18), substrate (19) FETSAAKLKRKYWWKNLK (SEQ ID NO: 19) and substrate (20) FETS(A+7)AKLKRKYWWKNLK (SEQ ID NO: 20). Substrate (15) (SEQ ID NO: 15) included the following peptide:

```
1  2  3  4  5  6  7  8  9  10 11 12 13 14 15 16 17
L  S  E  L  D  D  R  A  D  A  L  Q  A  G  A  S  Q
```

Substrate (16) (SEQ ID NO: 16) included the following peptide:

```
1 2 3 4 5 6 7 8          9 10 11 12 13 14 15 16 17
L S E L D D R (A + 7)    D  A  L  Q  A  G  A  S  Q
```

Substrate (17) (SEQ ID NO: 17) included the following peptide:

```
1  2  3  4  5  6  7  8  9  10 11 12 13 14 15 16
L  S  E  L  D  D  R  A  D  A  L  Q  A  G  A  S.
```

Substrate (18) (SEQ ID NO: 18) included the following peptide:

```
1 2 3 4 5 6 7 8          9 10 11 12 13 14 15 16
L S E L D D R (A + 7)    D  A  L  Q  A  G  A  S.
```

Substrate (19) (SEQ ID NO: 19) included the following peptide:

```
1  2  3  4  5  6  7  8  9  10 11 12 13 14 15 16 17 18
F  E  T  S  A  A  K  L  K  R  K  Y  W  W  K  N  L  K
```

Substrate (20) (SEQ ID NO: 20) included the following peptide:

```
1 2 3 4 5          6 7 8 9 10 11 12 13 14 15 16 17 18
F E T S (A + 7)    A K L K R  K  Y  W  W  K  N  L  K.
```

An example of a substrate for BoNT D and BoNT F includes: substrate (21) AQVDEVVDIMRVNVDKVLERDQKLSELDDRADALQAGAS (SEQ ID NO: 21). Isotope standards employed to calibrate and refine the method included: substrate (22) KLSELDDRADALQAGAS (SEQ ID NO: 22), substrate (23) KLSELDDR(A+7)DALQAGAS (SEQ ID NO: 23), substrate (24) AQVDEVVDIRVNVDKVLERDQ (SEQ ID NO: 24), substrate (25) (A+7) QVDEVVDIMRVNVDKVLERDQ (SEQ ID NO: 25), substrate (26) AQVDEVVDIMRVNVDKVLERDQK (SEQ ID NO: 26), and substrate (27) (A+7) QVDEVVDIMRVNVDKVLERDQK (SEQ ID NO: 27).

Substrate (21) (SEQ ID NO: 21) included the following peptide:

```
 1  2  3  4  5  6  7  8  9 10 11 12 13 14 15 16 17 18 19
 A  Q  V  D  E  V  V  D  I  M  R  V  N  V  D  K  V  L  E 20 21 22 23 24 25 26 27 28 29 30 31 32 33 34 35
 R  D  Q  K  L  S  E  L  D  D  R  A  D  A  L  Q 36 37 38 39
 A  G  A  S.
```

Substrate (22) (SEQ ID NO: 22) included the following peptide:

```
    1  2  3  4  5  6  7  8  9 10 11 12 13 14 15 16 17
    K  L  S  E  L  D  D  R  A  D  A  L  Q  A  G  A  S
```

Substrate (23) (SEQ ID NO: 23) included the following peptide:

```
 1  2  3  4  5  6  7  8  9          10 11 12 13 14 15 16 17
 K  L  S  E  L  D  D  R  (A + 7)     D  A  L  Q  A  G  A  S
```

Substrate (24) (SEQ ID NO: 24) included the following peptide:

```
 1  2  3  4  5  6  7  8  9 10 11 12 13 14 15 16 17 18 19
 A  Q  V  D  E  V  V  D  I  M  R  V  N  V  D  K  V  L  E 20 21 22
 R  D  Q
```

Substrate (25) (SEQ ID NO: 25) included the following peptide:

```
    1         2  3  4  5  6  7  8  9 10 11 12 13 14 15 16 17 18
 (A + 7)      Q  V  D  E  V  V  D  I  M  R  V  N  V  D  K  V  L 19 20 21 22
 E  R  D  Q
```

Substrate (26) (SEQ ID NO: 26) included the following peptide:

```
 1  2  3  4  5  6  7  8  9 10 11 12 13 14 15 16 17 18 19
 A  Q  V  D  E  V  V  D  I  M  R  V  N  V  D  K  V  L  E 20 21 22 23
 R  D  Q  K
```

Substrate (27) (SEQ ID NO: 27) included the following peptide:

```
    1         2  3  4  5  6  7  8  9 10 11 12 13 14 15 16 17 18
 (A + 7)      Q  V  D  E  V  V  D  I  M  R  V  N  V  D  K  V  L 19 20 21 22 23
 E  R  D  Q  K.
```

An example of a substrate for BoNT E includes: substrate (28) IIGNLRHMALDMGNEIDTQNRQIDRIMEKAD (SEQ ID NO: 28). Isotope standards employed to calibrate and refine the method included: substrate (29) IIGNLRHMALDMGNEIDTQNRQIDR (SEQ ID NO: 29), substrate (30) IIGNLRHM(A+7)LDMGNEIDTQNRQIDR (SEQ ID NO: 30), substrate (31) IMEKAD (SEQ ID NO: 31), and substrate (32) IMEK(A+7)D (SEQ ID NO: 32). Substrate (28) (SEQ ID NO: 28) included the following peptide:

```
 1  2  3  4  5  6  7  8  9 10 11 12 13 14 15 16 17 18 19
 I  I  G  N  L  R  H  M  A  L  D  M  G  N  E  L  D  T  Q 20 21 22 23 24 25 26 27 28 29 30 31
 N  R  Q  I  D  R  I  M  E  K  A  D
```

Substrate (29) (SEQ ID NO: 29) included the following peptide:

```
 1  2  3  4  5  6  7  8  9 10 11 12 13 14 15 16 17 18 19
 I  I  G  N  L  R  H  M  A  L  D  M  G  N  E  L  D  T  Q 20 21 22 23 24 25
 N  R  Q  I  D  R.
```

Substrate (30) (SEQ ID NO: 30) included the following peptide:

```
 1  2  3  4  5  6  7  8  9          10 11 12 13 14 15 16 17 18
 I  I  G  N  L  R  H  M  (A + 7)      L  D  M  G  N  E  I  D  T 19 20 21 22 23 24 25
 Q  N  R  Q  I  D  R.
```

Substrate (31) (SEQ ID NO: 31) included the following peptide:

```
       1  2  3  4  5  6
       I  M  E  K  A  D.
```

Substrate (32) (SEQ ID NO: 32) included the following peptide:

```
       1  2  3  4  5          6
       I  M  E  K  (A + 7)     D.
```

Examples of substrates for BoNT G include: substrate (33) IEYNVEHAVDYVERAVSDT-KKAVKYQSKARRKKINleI, substrate (34) IEYNVE-HAVDYVERAVSDTKKAVRYQSKARRKKINleI, substrate (35) IEYNVEHAVDYVERAVSQT-KKAVRYQSKARRKKINleI, and substrate (36) IEYNVE-HAVDYVERAVSQSKKAVRYQSKARRKKINleI. Substrate (33) (SEQ ID NO: 33) included the following peptide:

```
1 2 3 4 5 6 7 8 9 10 11 12 13 14 15 16 17 18 19
I E Y N V E H A V D  Y  V  E  R  A  V  S  D  T 20 21 22 23 24 25 26 27 28 29 30 31 32 33
 K  K  A  V  K  Y  Q  S  K  A  R  R  K  K 34 35 36
 I Nle I.
```

In this substrate at 35, Norleucine is substituted for Methionine,

```
1 2 3 4 5 6 7 8 9 10 11 12 13 14 15 16 17 18 19 20 21 22 23 24 25 26 27
                                                                          (SEQ ID NO: 65).
I E Y N V E H A V D  Y  V  E  R  A  V  S  D  T  K  K  A  V  K  Y  Q  S 28 29 30 31 32 33 34 35  36
 K  A  R  R  K  K  I Nle  I
```

Substrate (34) (SEQ ID NO: 34) included the following peptide:

```
1 2 3 4 5 6 7 8 9 10 11 12 13 14 15 16 17 18 19
I E Y N V E H A V D  Y  V  E  R  A  V  S  D  T 20 21 22 23 24 25 26 27 28 29 30 31 32 33
 K  K  A  V  R  Y  Q  S  K  A  R  R  K  K 34 35 36
 I  M  I.
```

In this substrate at 35, Norleucine is substituted for Methionine,

```
1 2 3 4 5 6 7 8 9 10 11 12 13 14 15 16 17 18 19 20 21 22 23 24 25 26 27   (SEQ ID NO: 66).
I E Y N V E H A V D  Y  V  E  R  A  V  S  D  T  K  K  A  V  R  Y  Q  S 28 29 30 31 32 33 34 35  36
 K  A  R  R  K  K  I Nle  I
```

Substrate (35) (SEQ ID NO: 35) included the following peptide:

```
1 2 3 4 5 6 7 8 9 10 11 12 13 14 15 16 17 18 19
I E Y N V E H A V D  Y  V  E  R  A  V  S  Q  T 20 21 22 23 24 25 26 27 28 29 30 31 32 33
 K  K  A  V  R  Y  Q  S  K  A  R  R  K  K 34 35 36
 I  M  I.
```

In this substrate at 35, Norleucine is substituted for Methionine,

```
 1  2  3  4  5  6  7  8  9 10 11 12 13 14 15 16 17 18 19 20 21 22 23 24 25 26 27     (SEQ ID NO: 67).
 I  E  Y  N  V  E  H  A  V  D  Y  V  E  R  A  V  S  Q  T  K  K  A  V  R  Y  Q  S 28 29 30 31 32 33 34 35  36
 K  A  R  R  K  K  I  Nle  I
```

Substrate (36) (SEQ ID NO: 36) included the following peptide:

```
 1  2  3  4  5  6  7  8  9 10 11 12 13 14 15 16 17 18 19 20
 I  E  Y  N  V  E  H  A  V  D  Y  V  E  R  A  V  S  Q  S  K 21 22 23 24 25 26 27 28 29 30 31 32 33 34 35 36
 K  A  V  R  Y  Q  S  K  A  R  R  K  K  I  M  I.
```

In this substrate at 35, Norleucine is substituted for Methionine,

```
 1  2  3  4  5  6  7  8  9 10 11 12 13 14 15 16 17 18 19 20 21 22 23 24 25 26 27

(SEQ ID NO: 68).
 I  E  Y  N  V  E  H  A  V  D  Y  V  E  R  A  V  S  Q  S  K  K  A  V  R  Y  Q  S 28 29 30 31 32 33 34 35  36
 K  A  R  R  K  K  I  Nle  I
```

Amides of the BoNT substrates, which can be more stable towards C terminal degradation in solution, are easily incorporated into the assay. Examples include substrate (37) SNKTRIDEANQRATKML-amide (SEQ ID NO: 37) and substrate (38) SNRTRIDEANQRATRML-amide (SEQ ID NO: 38). Substrate (37) (SEQ ID NO: 37) included the following peptide with amide bound at one end of the peptide:

```
 1  2  3  4  5  6  7  8  9 10 11 12 13 14 15 16 17

S  N  K  T  R  I  D  E  A  N  Q  R  A  T  K  M  L.
```

Substrate (38) (SEQ ID NO: 38) included the following peptide with amide bound at one end of the peptide:

```
 1  2  3  4  5  6  7  8  9 10 11 12 13 14 15 16 17

S  N  R  T  R  I  D  E  A  N  Q  R  A  T  R  M  L.
```

MAP$_4$ like tree structures have been synthesized and shown to increase the specific turnover, over unspecific protease background cleavage reactions, for example, substrate (39) (SNRTRIDQGNQRATRNleL)4K2KC(beta)A (SEQ ID NO: 39), a Lysine MAP$_4$ tree. Substrate (39) (SEQ ID NO: 39) included the following peptide with a lysine MAP$_4$ structure tree bound at the C-end of the peptide:

```
 1  2  3  4  5  6  7  8  9 10 11 12 13 14 15 16 17

S  N  R  T  R  I  D  Q  G  N  Q  R  A  T  R  M  L.
```

In this substrate at 16, Norleucine is substituted for Methionine,

```
                                                          (SEQ ID NO: 69).
 1  2  3  4  5  6  7  8  9 10 11 12 13 14 15  16  17
 S  N  R  T  R  I  D  Q  G  N  Q  R  A  T  R  Nle  L
```

Peptide sequences for the BoNT endoproteinase assay are listed in Table 1 along with the predicted cleavage products for each serotype, and masses associated with the substrate and cleaved product peptides. Superscript letters in the sequence denote the cleavage site for the serotype, e.g., $^a$=BoNT-A. The peptides for BoNT-A, -C, and -E were derived from the human SNAP-25 protein. The BoNT-A/-C substrate (1) has modifications from the native human SNAP-25 sequence (187-substrate 37-203) for the BoNT-A/-C substrate of biotin($\epsilon$)-KG(K$_{189}$->R and K$_{201}$->R)GGK-($\epsilon$)Biotin. The BoNT-E substrate sequence (2) was also from human SNAP-25 (156-186). The substrate peptides for BoNT-B, -D, and -F are from human synaptobrevin 2; the BoNT-B substrate (3) is from 59-93 in the sequence and the BoNT-D/-F substrate is from 35-74.

TABLE 1

Substrates and Corresponding Fragments

| | Botulinum Neurotoxin Specific Peptide Substrates | Mass |
|---|---|---|
| BoNT-A, -C | Biotin-KGSNRTRIDEANQ$^a$R$^c$ATRMLGGK-Biotin (Substrate 1) | 2912.6 |
| NT-BoNT-A Product | Biotin-KGSNRTRIDEANQ$^a$ | 1713.8 |
| GT-BoNT-A Product | $^a$RATRMLGGK-Biotin | 1215.3 |
| NT-BoNT-C Product | Biotin-KGSNRTRIDEANQR$^c$ | 1871.0 |
| CT-BoNT-C Product | $^c$ATRMLGGK-Biotin | 1059.6 |
| BoNT-E | IIGNLRHMALDMGNEIDTQNRQIDR$^e$IMEKAD (Substrate 28) | 3612.1 |
| NT-BoNT-E Product | IIGNLRHMALDMGNEIDTQNRQIDR$^e$ | 2924.3 |
| CT-BoNT-E Product | $^e$IMEKAD | 705.8 |
| BoNT-B | LSELDDRADALQAGASQ$^b$FETSAAKLKRKYWWKNLK (Substrate 14) | 4039.6 |
| NT-BoNT-B Product | LSELDDRADALQAGASQ$^b$ | 1759.8 |
| CT-BoNT-B Product | $^b$FETSAAKLKRKYWWKNLK | 2297.7 |
| BoNT-D, -F | AQVDEVVDIMRVNVDKVLERDQ$^f$K$^d$LSELDDRADALQAGAS (Substrate 21) | 4312.8 |
| CT-BoNT-D Product | AQVDEVVDIMRVNVDKVLERDQK$^d$ | 2699.1 |
| NT-BoNT-D Product | $^d$LSELDDRADALQAGAS | 1631.7 |
| NT-BoNT-F Product | AQVDEVVDIMRVNVDKVLERDQ$^f$ | 2570.9 |
| GT-BoNT-F Product | $^f$KLSELDDRADALQAGAS | 1759.9 |
| Internal Standard | LRTAQADITNSK-(ε) Biotin | 1542.78 |
| BoNT-A | SNRTRIDQGNQRATRXL (X = norleucine) (Substrate 40) | 1998.3 |
| NT-BoNT-A Product | SNRTRIDQGNQ | 1288.3 |
| CT-BoNT-A Product | RATRXL | 729.5 |

(SEQ ID NO: 40) Fragment 1 from Substrate 1, KGSNRTRIDEANQ. Fragment 1 includes Biotin that is bound at the first terminous of the protein fragment.
(SEQ ID NO: 41) Fragment 2 from Substrate 1, RATRMLGGK. Fragment 2 includes Biotin that is bound at no. 9 of the protein fragment.
(SEQ ID NO: 42) Fragment 3 from Substrate 1, KGSNRTRIDEANQR Fragment 3 includes Biotin that is bound at the first terminous of the protein fragment.
(SEQ ID NO: 43) Fragment 4 from Substrate 1, ATRMLGGK. Fragment 4 includes Biotin that is bound at no. 8 of the protein fragment.
(SEQ ID NO: 44) Fragment 5 from Substrate 28, IIGNLRHMALDMGNEIDTQNRQIDR.
(SEQ ID NO: 45) Fragment 6 from Substrate 28, IMEKAD.
(SEQ ID NO: 46) Fragment 7 from Substrate 14, LSELDDRADALQAGASQ.
(SEQ ID NO: 47) Fragment 8 from Substrate 14, FETSAAKLKRKYWWKNLK.
(SEQ ID NO: 48) Fragment 9 from Substrate 21, AQVDEVVDIMRVNVDKVLERDQK.
(SEQ ID NO: 49) Fragment 10 from Substrate 21, LSELDDRADALQAGAS.
(SEQ ID NO: 50) Fragment 11 from Substrate 21, AQVDEVVDIMRVNVDKVLERDQ.
(SEQ ID NO: 51) Fragment 12 from Substrate 21, KLSELDDRADALQAGAS.
(SEQ ID NO: 52) LRTAQADITNSK. Biotin is bound at no. 12 of the protein fragment.
(SEQ ID NO: 53) Substrate 40, SNRTRIDQGNQRATRXL. (X=norleucine)
(SEQ ID NO: 54) Fragment 13 from Substrate 40, SNRTRIDQGNQ.
(SEQ ID NO: 55) Fragment 14 from Substrate 40, RATRXL.

Affinity tags such as biotin are attached on both sides of the cleavage site on the substrate such that after cleavage the products from the cleavage can be collected and separated from any matrix and sample contaminants, as well as, from the toxins. The recovery of both unreacted substrate and cleavage products can be used for calibration and control experiment purposes.

The mass spectroscopy approach to analysis of the products allows a quantification of the amount of neurotoxin since the ratio of the products to the unreacted substrate can be determined, the length of time of digestion will be known and the amount of starting material, i.e., substrate, will be known so that a calibration curve may be calculated and allow the quantification of the amount of neurotoxin.

The ENDOPEP-MS reaction has proven to be very useful for detecting small amounts of BoNT in a rapid, animal-free assay. This assay is very effective when used as a 20 μL reaction consisting of BoNT, reaction buffer, and peptide substrate, with detection of the cleavage of the peptide substrate through mass spectrometry. However, there may be a need to perform this assay with clinical samples in larger volumes (100 μL to 1 mL) and such an additional step may be preferred in those instances. Many food and clinical samples contain abundant proteases which cleave the peptide substrate, prohibiting the toxin from cleaving the substrate. Therefore, it becomes necessary to pursue a method to capture and concentrate BoNT from a larger volume (100 μL to 1 mL) of a clinical or other type of sample. It has now been shown that the use of antibodies is extremely effective at concentrating the toxin while discarding proteases which have a detrimental effect on the assay. In this method, antibody (Ab) is bound to magnetic protein G beads which are then cross-linked to the beads to ensure their attachment and proper orientation. It should be noted that antibody platforms other than magnetic beads, such as columns or pipette tips would also most likely work as well. After washing the cross-linked Ab-coated beads, the beads are blocked through the addition of casein buffer and a short incubation. Upon removal of the casein buffer, toxin in a liquid matrix (buffer, milk, serum, stool extract, food extract, or gastric extract) can be added to the Ab-coated beads and incubated for 2 hours while the toxin present in the sample binds to the Ab-coated beads and other proteases do not. The beads can then be stringently washed with a detergent-containing buffer followed by a water wash to dispose of the detergent. At this point, the reaction buffer and the peptide substrate are added to the Ab-coated beads for an incubation of several hours. If toxin is present, the peptide substrate is cleaved in a specific location, generating two product peptides. These product peptides can then be detected through analysis by mass spectrometry.

As noted, the ENDOPEP-MS reaction has proven to be very useful for detecting small amounts of BoNT in a rapid, animal-free assay and the assay is very effective when used as a 20 µL reaction consisting of BoNT, reaction buffer, and peptide substrate, with detection of the cleavage of the peptide substrate through mass spectrometry. However, when working with clinical or food samples, there are abundant proteases which cleave either the peptide substrate or other proteases, producing a large number of uninteresting peptides. Because mass spectrometers detect peptides based on their ionization efficiencies, it is critical to analyze a sample which preferentially contains an enriched sample of the peptides of interest in order for those peptides to ionize at their optimum level. Therefore, an affinity method of selecting for the peptides generated from the cleavage of the peptide substrate by BoNT may be preferentially used for ultimate detection in complex biological samples. Biotinylated peptides have been used in conjunction with avidin affinity chromatography to purify the peptides prior to the mass spectrometric analysis. It should be noted that other tagging platforms could be used here as well such as, e.g., fluorous tagged peptides (a peptide tagged with a fluorous compound such as those described, e.g., in U.S. Pat. No. 6,803,475); however, the avidin-biotin bond was chosen as it is one of the strongest bonds in biology. Conditions were optimized on synthetic product peptides using avidin columns, although it should be noted that other avidin-biotin platforms could be used as well, such as biotinylated peptides with avidin-coated beads. The reactions with BoNT and the biotinylated peptides were allowed to proceed from 4 to 24 hours and the reaction mixtures were diluted in buffer and applied to the avidin columns. The bound substrate and product peptides were then eluted. This procedure works very well to clean-up the product peptides of interest from complex matrices.

The peptide substrates used in the present method were designed to be the same as the sequences of those portions of the natural SNAP-25 (for BoNT A and E) or VAMP (for BoNT B and F) that are recognized and cleaved, except some modifications were made in the substrate peptide for BoNT A. Other modifications allowing better stability may be conducted as well. For BoNT A the peptide from SNAP-25 that includes serine-187 to glycine-206 is required for cleavage at glutamine-196. James Schmidt et al., Appl. Env. Microbiol., v. 69(1), pp. 297-303 (2003) previously found that certain modifications to the natural sequence of this SNAP-25-derived peptide showed enhanced cleavage by BoNT A. Modifications that enhanced cleavage by BoNT A included replacing lysines 189 and 201 with arginines. This modification was made to the substrate peptide for BoNT A and resulted in an increase in the amount of BoNT-dependent cleavage products detected, over that observed with an unmodified SNAP-25 based peptide. The portion of VAMP-2 that is required for cleavage by BoNT B at glutamine-75 is leucine-59 to lysine 93 and the portion required for cleavage by BoNT F at glutamine-57 is from alanine-36 to serine-74. The portion of SNAP-25 from isoleucine-156 to aspartic acid-186 is required for cleavage between arginine-180 and isoleucine-181 by BoNT E. Possible modifications to the substrate peptides for B, E and F are being explored that may enhance BoNT cleavage. The N and C terminus of the substrate peptide for BoNT A have also been biotinylated so that the product peptides of interest can be easily purified from complex matrices. After final peptide sequences are determined, all of the substrate peptides may be biotinylated or derivatized by other suitable affinity tags for specific application requirements.

Figure 2:
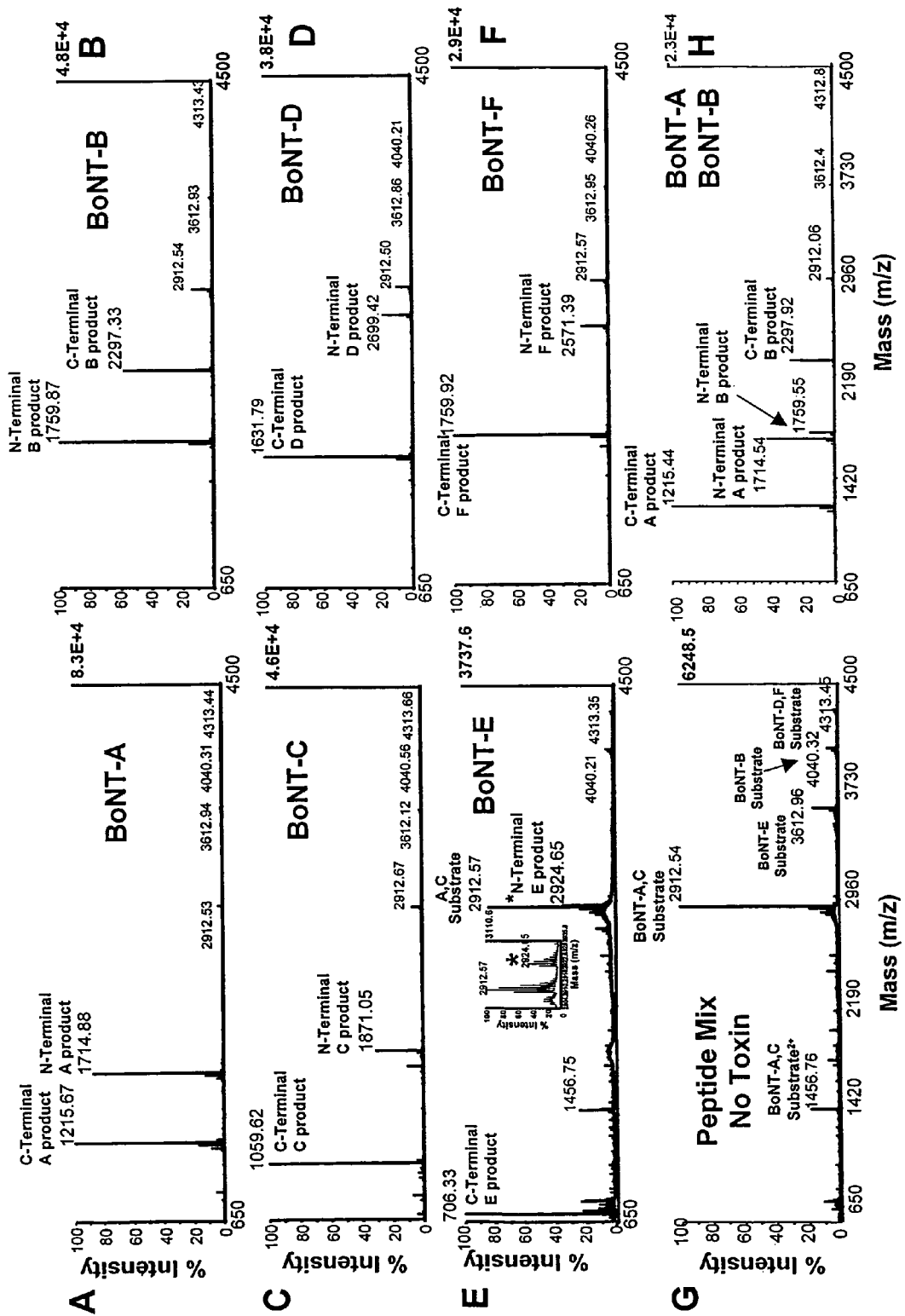
FIG. 2 shows four peptides: (1) Substrate 1-Biotin($\epsilon$)-KG-SNRTRIDEANQRATRMLGGK-($\epsilon$)Biotin (SEQ ID NO: 1); (2) Substrate 14 -LSELDDRADALQAGASQFETSAAK-LKRKYWWKNLK (SEQ ID NO: 14); (3) Substrate 21-AQVDEVVDIMRVNVDKVLERDQKLSELD-DRADALQAGAS (SEQ ID NO: 21); and (4) Substrate 28-IIGNLRHMALDMGNEIDTQNRQIDRIMEKAD (SEQ ID NO: 28), at 1 nmole each in BoNT- reaction buffer containing 0.05 M Hepes pH 7.3, 25mM DTT, 20 mM $ZnCl_2$, and 1 mg/ml BSA were spiked with BoNT-A (A), BoNT-B (B), BoNT-C (C), BoNT-D (D), BoNT-E (E), BoNT-F (F), $dH_2O$ for no toxin (G), BoNT-A and BoNT-B (H). The toxins were spiked at 200 ng and incubated for 2 hours at 37° C. Each reaction (1 µl) was spiked into 9 µl of 5 mg/ml alpha-cyano-4-hydroxy-cinnamic acid in 50% acetonitrile, 0.1% TFA, 1 mM ammonium citrate, then spotted in triplicate onto a MALDI plate. Mass spectra were obtained by MALDI-TOF MS over the mass/charge (m/z) range from 650 to 4500. The inset mass spectra for BoNT-E distinguishes the NT-BoNT-E product from the BoNT-A substrate.

The method was multiplexed by combining all four substrate peptides for the BoNT serotypes A, B, E, and F into a sample that contained various levels of a single BoNT serotype or no toxin. The samples were incubated for 2 hours and the resulting peptides were measured by either MALDI-TOF-MS or LC/ESI/MS/MS. The expected product peptide masses along with the masses of the substrate peptides are shown in FIG. 2. The product peptides for each specific BoNT serotype can be easily distinguished by their mass. Typical results for each of the reaction mixtures containing the four substrate peptides incubated with only the reaction buffer (a blank) or with one of the BoNT serotypes showed that each of the BoNT serotypes only yielded the expected cleavage products from their respective substrate peptides indicating that this method can easily detect and differentiate active BoNT serotypes.

The sensitivity of the method was also tested. For BoNT A, B, and F, as little as 0.01 mouse $LD_{50}$ (about 0.1 pg active toxin) of BoNT in a sample can yield sufficient quantities of product peptides to be clearly detected by MALDI-TOF-MS. This is 100 times lower than can be detected by the mouse bioassay. Additionally, this small amount of toxin can be detected and the toxin type differentiated in a single measurement. The mouse bioassay would require separate mice for each of the toxin types to differentiate the BoNT serotype.

This method is currently less sensitive for BoNT E than the other serotypes. One mouse $LD_{50}$ is required to clearly detect the product peptides by MALDI-TOF-MS; however, the activity of BoNT E can be enhanced by tryptic activation of the toxin. The *Clostridium botulinum* strains that produce BoNT E lack the proteases that are required to process the toxin into its highly active form. This activation presumably occurs in vivo in individuals with botulism from BoNT E. The mouse bioassay generally includes some trypsin-activated samples in conjunction with non-activated samples for injecting into the mouse. Additional work on this step in the ENDOPEP-MS method may enhance the sensitivity of the method for BoNT E.

The ENDOPEP-MS method has been applied to a variety of matrices spiked with specific BoNT serotypes and also tested blank samples that contain no BoNT. This method has been able to detect active BoNT serotypes in all of the food and clinical samples which include milk, yogurt, cheese, beef, sausage, serum, and stool. The sensitivities in these matrices ranged from 0.01 in milk to 10 mouse $LD_{50}$ in stool and meat. In these samples endogenous proteases can diminish the amount of intact substrate peptides and can destroy some of the intact product peptides. It is important to note that no other proteases have been found in any matrix that cleaves at the same site as the BoNT A, B, and F serotypes. The MS detection method is so specific that the exact site of cleavage can easily be determined. Thus, no false positives were obtained in any of the matrices. Endogenous proteases merely diminish the absolute sensitivity of the method. This level of specificity cannot easily be obtained in any fluorescence-based detection system and false positives would be expected with activity-based methods that employ flourescence or flourigenic systems. Work continues on the use of simple physical and chromatographic methods in combination with cocktails of protease inhibitors to obtain the best sensitivity in meat and stool samples; however, the amount of BoNT in a contaminated meat or stool sample would likely be much higher than 10 mouse $LD_{50}$, thus allowing detection with the present method. Pre-assay enrichment of the botulinum toxins can further enhance the selectivity over unspecific substrates.

The quantification of the amount of active BoNT in a sample is important. MALDI-TOF-MS is very rapid and is appropriate for relative quantification, but has limited capability for absolute quantification since the spectra tend to show larger variations than other mass spectral techniques. Thus, a LC-ESI/MS/MS technique that can quantitatively detect and differentiate BoNT activities has been developed. This method is highly specific, since correct identification of the BoNT product peptides depends on both a retention time match with respect to standards, and on a chemical-specific fragmentation (a precursor to product ion multiple reaction monitoring (MRM) transition) monitored by tandem MS. To further enhance specificity, two separate MRM transitions are monitored for each peptide. In addition, the LC-ESI/MS/MS technique can be very sensitive, because it uses a triple quadrupole-based instrument. Absolute quantification of the BoNT product peptides is achieved using leucine enkephalin (any other stable peptide which is neither a substrate nor an inhibitor of the BoNT reaction may be used) as an internal standard to correct for any instrumental variations. Typical LC-ESI/MS/MS chromatograms were obtained during the quantification of the activity of BoNT A, along with a standard curve for one of the product peptides. Based on obtained data, it is estimated that it should be possible to achieve absolute quantification to within less than 10-20% of the true BoNT activity level. Identical LC-ESI/MS/MS strategies can be used to quantify each of the BoNT serotypes. The amount of product peptides produced in a BoNT reaction may be correlated to the amount of active toxin in the sample.

The ENDOPEP-MS method has many possible applications. It was developed for the rapid detection and differentiation of BoNT in human clinical samples. Because it is rapid and sensitive, it could also be used to test food samples for BoNT. Beyond using the ENDOPEP-MS method for identifying the BoNT serotype in a clinical, food or environmental sample, it may be possible to standardize BoNT activity in samples used for clinical treatment or in research activities. The standardization of BoNT, both the amount of 150 KDa toxin and the activity of a standard solution, is of great importance in the use of BoNT medically and in the search for inhibitors of BoNT and treatments for botulism.

The present invention is more particularly described in the following examples which are intended as illustrative only, since numerous modifications and variations will be apparent to those skilled in the art.

EXAMPLE 1

Peptidic substrates were obtained using standard solid state peptide synthesis. A C-terminal biotin was obtained using a commercial Lysine(K)-biotin resin (available from Advanced Chem. Tech.) and standard solid state peptide synthesis conducted to construct the desired substrate with the N-terminal biotin introduced onto the peptide on a Boc-lysine (Fmoc) terminus after deprotection of the sidechain using commercially available activated biotin succinimide (available from NovaBiochem). In this manner the peptidic substrate of Biotin-KGSNRTRIDEANQRATRMLGGK-biotin (SEQ ID NO: 1) (Substrate 1) was prepared.

EXAMPLE 2

An initial sample of the peptide Biotin-KGSNRTRIDE-ANQRATRMLGGK-biotin (SEQ ID NO: 1) (Substrate 1) was measured by MALDI-TOF-MS. The mass spectroscopy data of this sample is shown in FIG. 1(a).

The sample of the peptide Biotin-KGSNRTRIDEAN-QRATRMLGGK-biotin (SEQ ID NO: 1) (Substrate 1) was then mixed with a sample of BoNT serotype A and the mixture was digested for two hours and the peptide substrate and products were specifically absorbed on avidin affinity columns, washed and then eluted with free biotin. The collected sample was then analyzed by MALDI-TOF-MS. The mass spectroscopy data of this sample is shown in FIG. 1(b). Two distinct peptide products were shown that were the result of the specific cleavage of the peptide. Excess biotin had a lower molecular weight outside the range of this MS range. Quantification of the amount of neurotoxin from the known quantities, time of digestion and MS data indicated detection of activity as low as 5 pc/mL of toxin.

EXAMPLE 3

As noted, the ENDOPEP-MS reaction has proven to be very useful for detecting small amounts of BoNT in a rapid, animal-free assay. The use of antibodies in concentrating the toxin can be conducted as follows.

Antibodies can be obtained from a variety of sources, e.g., Metabiologics (Madison, Wis.) supplies antibodies in a solution of 150 mM potassium phosphate, pH 7.4. The concentration for each batch of antibody is different. Magnetic protein G beads can be obtained from Dynal (Lake Success, N.Y.) at 1.3 g/cm³ and are supplied in a solution of phosphate buffered saline (PBS), pH 7.4, containing 0.1% Tween TWEEN®-20 (polyoxyethylene sorbitan monolaurate)and 0.02% sodium azide. Triethanolamine and dimethyl pimelimidate used for cross-linking can be obtained from Sigma-Aldrich (St. Louis, Mo.). Casein buffer is comprised of 5 g of casein (Sigma-Aldrich) dissolved in 500 mL of PBS (Sigma-Aldrich). PBS-T buffer is comprised of PBS with 0.005% TWEEN ®-20 (Sigma-Aldrich). TBS buffer is comprised of Tris buffer saline (50 mM Tris buffer with 10 mM NaCl at pH=7.5) obtained from Sigma-Aldrich. Protease inhibitor cocktail is comprised of 5% casein, 4.5 mg/mL of 4-(2-Aminoethyl)benzenesulfonyl fluoride hydrochloride (AEBSF), 25 mg/mL of 6-Aminohexanoic acid, 3.15 mg/mL of Antipain, and 20 mg/mL of (2S,3S)-trans-Epoxysuccinyl-L-leucylamido-3-methylbutane ethyl ester (E-64). All protease inhibitors can be obtained from Sigma-Aldrich.

The manufacture of antibody-coated beads can be as follows.

1) Transfer 100 μL of protein G magnetic beads into a microcentrifuge tube.
2) Place the tube on the magnet for 30 seconds and pipette off the supernatant.
3) Remove the tube from the magnet and add 500 μL of PBS buffer. Reconstitute the beads so that a homogeneous solution is formed.
4) Repeat steps 3, 4, and 3.
5) Put 50 μg of antibody into 500 μL of PBS and add this solution to the beads.
6) Incubate this mixture at room temperature on a rotation device for several hours.
7) Place the tube with the beads on the magnet for 30 seconds and pipette off the supernatant.

8) Remove the tube from the magnet and add 500 µL of PBS buffer.
9)
10) Repeat steps 7 and 8 twice.
11) Place the tube on the magnet and pipette off the supernatant.
12) Add 1 mL of triethanolamine buffer to the beads. Reconstitute the beads so that a homogeneous solution is formed.
13) Place the tube with the beads on the magnet for 30 seconds and pipette off the supernatant.
14) Repeat steps 11 and 12.
15) Mix a solution of 5.4 mg of dimethyl pimelidate in 1 mL of triethanolamine buffer. Add this solution to the beads.
16) Incubate this mixture at room temperature on a rotation device for 30 minutes.
17) Place the tube with the beads on the magnet for 30 seconds and pipette off the supernatant.
18) Re-suspend the beads in 1 mL of TBS buffer and incubate for 15 minutes at room temperature on a rotation device.
19) Place the tube on the magnet for 30 seconds and pipette off the supernatant.
20) Reconstitute the beads in 500 µL of PBS-T.
21) Repeat steps 18 and 19.
22) Place the tube on the magnet for 30 seconds and pipette off the supernatant.
23) Reconstitute the beads in 100 µL of PBS-T and store until needed.

The capture of toxin with antibody-coated beads can be as follows.
1) Prepare toxin-spiked sample by adding BoNT to liquid sample and set aside.
2) Prepare beads for capture by using beads at ⅕ the volume of the sample (e.g. if sample size is 500 µL, use 100 µL of beads).
3) Add liquid toxin-spiked sample to the beads.
4) If toxin-spiked sample is serum, stool extract, food extract, or gastric extract, add protease inhibitor cocktail at 1/20 the volume of the sample (e.g. if sample size is 500 µL, use 25 µL of protease inhibitor cocktail).
5) Incubate at room temperature for 2 hours on a rotation device.
6) Place the tube with the beads on the magnet for 30 seconds and pipette off the supernatant.
7) Add 500 µL of PBS-T buffer to the beads and reconstitute them.
8) Repeat steps 5 and 6 three times.
9) Place the tube with the beads on the magnet for 30 seconds and pipette off the supernatant.
10) Add 500 µL of water to the beads and reconstitute them.
11) Repeat steps 8 and 9.
12) Place the tube with the beads on the magnet for 30 seconds and pipette off the supernatant.
13) Reconstitute the beads in 19 µL of reaction buffer and 1 µL of peptide substrate for all samples other than stool extract. For stool extract samples, add 16.5 µL of reaction buffer, 1 µL of peptide substrate, and 2.5 µL of protease inhibitor cocktail.
14) Incubate BoNT reaction and analyze substrate cleavage by mass spectrometry of supernatant.

EXAMPLE 4

As noted, the ENDOPEP-MS reaction has proven to be very useful for detecting small amounts of BoNT in a rapid, animal-free assay. The use of affinity chromatography in purifying the toxin can be conducted as follows. This procedure worked very well to clean-up the product peptides of interest from complex matrices.

All chemicals for this example were obtained from Sigma-Aldrich (St. Louis, Mo.) unless otherwise noted.
1) Biotinylated peptides were constructed using standard solid state peptide synthesis to yield the desired substrate.
2) Avidin columns were obtained from Applied Biosystems (Foster City, Calif.) as a portion of the ICAT kit. It should be noted that avidin columns from other sources could be used as well.
3) Load buffer is phosphate buffered saline (PBS) at a 2× concentration, diluted from a 10× concentration, which is 100 mM sodium phosphate, 9% NaCl, pH=7.4.
4) Wash #1 buffer is PBS at a 1× concentration, diluted from a 10× concentration.
5) Wash #2 buffer is 50 mM ammonium bicarbonate, 20% methanol.
6) Elution buffer is 30% acetonitrile and 0.4% trifluoroacetic acid (TFA)
7) Storage buffer is PBS at 1× concentration with 0.1% sodium azide.
8) Matrix solution is alpha-cyano-4-hydroxy cinnamic acid (CHCA) at 5 mg/mL in 50% acetonitrile, 0.1% TFA, and 1 mM ammonium citrate The purification method was as follows.
1) The 20 uL BoNT reaction was diluted to 500 uL in load buffer and set aside until needed.
2) 1 mL of the elution buffer was pushed through the avidin column.
3) 2 mL of the load buffer was pushed through the avidin column.
4) The 500 uL sample was then pushed through the avidin column.
5) 1 mL of wash #1 buffer was pushed through the avidin column.
6) 1 mL of wash #2 buffer was pushed through the avidin column.
7) 50 uL of elution buffer was then pushed through the avidin column.
8) 750 uL of elution buffer was then pushed through the avidin column and this eluent was collected and set aside until needed.
9) 2 mL of additional elution buffer was pushed through the avidin column.
10) 2 mL of load buffer was pushed through the avidin column.
11) 2 mL of storage buffer was pushed through the avidin column which was then stored at 4° C. until needed again.
12) The 750 uL fraction was lyophilized to dryness and reconstituted in 10 uL of matrix solution.
13) The sample and matrix mixture was applied to a MALDI plate and analyzed by MALDI-TOF MS using a 4700 Proteomics analyzer (Applied Biosystems).

EXAMPLE 5

For the ENDOPEP-MS method, BoNTs A, B, E, and F proteolytic activities were determined in 20-uL volumes containing 0.05 M Hepes, pH 7.3, 25 mM DTT, 20 mM $ZnCl_2$ (reaction buffer) 1 mg/mL bovine serum albumin (BSA) along with the target peptides, at 1 nmole each. Specific BoNT serotype complexes were added at various concentrations, and incubated at 37° C. for 2 hours to overnight. Control tubes with no BoNT were also run at the same time as the BoNT cleavage reactions and served as an analytical blank. Endopeptidase reactions were multiplexed by adding all four peptides (1-4) at 1 nmole each, to the reaction buffer described above. BoNT-A titrated from 100 to 0.01 U/μL was spiked at 1 μL in reaction buffer alone and with 1 μL milk, yogurt, cheese, beef, sausage, serum, and stool.

Specific cleavage products were detected by mass spectrometry. For all experiments, the reaction mixture, at the incubation times indicated, was added to alpha-cyano-4-hydroxy cinnamic acid (CHCA) at 5 mg/ml in 50% acetonitrile, 0.1% trifluoroacetic acid, and 1 mM ammonium citrate (CHCA matrix), at a ratio of 1:5 or 1:10. This mix was applied at 0.5 μL per spot to a 192 spot MALDI plate (Applied Biosystems, Framingham, Mass.). Mass spectra of each spot were obtained by scanning from 650 to 4500 m/z in MS positive ion reflectron mode on a Model 4700 MALDI-TOF-MS Proteomics Analyzer (Applied Biosystems, Toronto, Canada). The instrument used a nitrogen laser at 337 nm and each spectrum was an average of 2400 laser shots.

The LC-ESI/MS/MS system consisted of an API4000 triple quadrupole mass spectrometer with a standard TurboIonSpray® interface (Applied Biosystems, Toronto, Canada) and a Shimadzu (Kyoto, Japan) liquid chromatograph. Luna C18 (Phenomenex, Torrance, Calif., USA) columns (150 mm×1 mm I.D., 5 μm particles) were used. Solvents were A: $H_2O$ with 1% (v/v) formic acid and B: 80:20 acetonitrile:$H_2O$ plus 1% (v/v) formic acid. Peptides were eluted with a linear gradient of 0 to 80% solvent B in 25 minutes, at 50 μL/min. A parallel column format was used, giving a cycle time of 34 minutes. Tandem MS was performed by monitoring two precursor to product transitions under individually optimized conditions, typically from the most abundant $[M+nH]^{n+}$ precursor ion to an immonium ion. Leucine enkephalin ($[M+H]^+$556) was used as an internal standard for quantification of BoNT product peptides.

Although the present invention has been described with reference to specific details, it is not intended that such details should be regarded as limitations upon the scope of the invention, except as and to the extent that they are included in the accompanying claims.

What is claimed is:

1. A method for detecting the presence of clostridial botulinum neurotoxins in a sample comprising the steps of:
   a) mixing a sample that may comprise serotypes of clostridial neurotoxins with a peptide substrate, wherein said peptide substrate is KGSNRTRIDEANQRATRM-LGGK-(SEQ ID NO: 1), and optionally, one or more peptide substrates selected from the group consisting of SEQ ID NO:14, 21, and 28, for proteolytic activity of said clostridial neurotoxin serotypes, such that at least a portion of the amount of the substrate is proteolytically cleaved by a serotype to produce a mixture comprising uncleaved substrate and peptide cleavage products;
   b) analyzing the mixture on a mass spectrometer to produce a signal corresponding to the mass of at least one peptide cleavage product;
   c) using the signal corresponding to the peptide cleavage products to identify the clostridial neurotoxin serotype;
   d) quantitating the amount of proteolytic cleavage of the peptide substrate for the clostridial neurotoxin serotype by stable isotope dilution mass spectrometry.

2. The method of claim 1 wherein said peptide substrate has an affinity tag attached at two or more sites.

3. The method of claim 1 wherein said botulinum neurotoxin is selected from the group consisting of serotype A, serotype B, serotype C, serotype D, serotype E, serotype F, serotype G, and mixtures thereof.

4. The method of claim 1 wherein said botulinum neurotoxin is of serotype A.

5. The method of claim 1 wherein said botulinum neurotoxin is of serotype B.

6. The method of claim 1 wherein said botulinum neurotoxin is of serotype E.

7. The method of claim 1 wherein said botulinum neurotoxin is of serotype F.

8. The method of claim 2 wherein said affinity tag is biotin.

9. The method of claim 2 wherein said affinity tag is a fluorous compound.

10. The method of claim 2, further comprising the step of recovery of uncleaved substrate and peptide cleavage products via said affinity tags.

11. The method of claim 1, wherein the sample is a biological sample comprising food, serum, stool, or combinations thereof.

12. The method of claim 1 wherein said botulinum neurotoxin comprises a mixture of at least two serotypes selected from the group consisting of serotype A, serotype B, serotype C, serotype D, serotype E, serotype F, serotype G, and mixtures thereof.

13. The method of claim 1 wherein said botulinum neurotoxin comprises a mixture of at least three serotypes selected from the group consisting of serotype A, serotype B, serotype C, serotype D, serotype E, serotype F, serotype G, and mixtures thereof.

* * * * *